US00PP36138P2

(12) United States Plant Patent
Wood

(10) Patent No.: US PP36,138 P2
(45) Date of Patent: Sep. 24, 2024

(54) ***PHYSOCARPUS* PLANT NAMED 'SMPOCGT'**

(50) Latin Name: *Physocarpus opulifolius*
Varietal Denomination: SMPOCGT

(71) Applicant: Spring Meadow Nursery, Inc., Grand Haven, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 18/541,467

(22) Filed: Dec. 15, 2023

(51) Int. Cl.
*A01H 5/02* (2018.01)
*A01H 6/74* (2018.01)

(52) U.S. Cl.
USPC ..... Plt./226
CPC ..... *A01H 6/74* (2018.05)

(58) Field of Classification Search
USPC ..... Plt./226
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Physocarpus* plant named 'SMPOCGT' is disclosed, characterized by red-orange spring leaves, turning dark maroon with green undersides in summer. Plants have bright red stems, and light pink to white flowers producing bright reddish-pink seed heads. Plants produce bright red fruit. The new cultivar is a *Physocarpus*, normally produced as an outdoor garden or container plant.

3 Drawing Sheets

Figure 1:
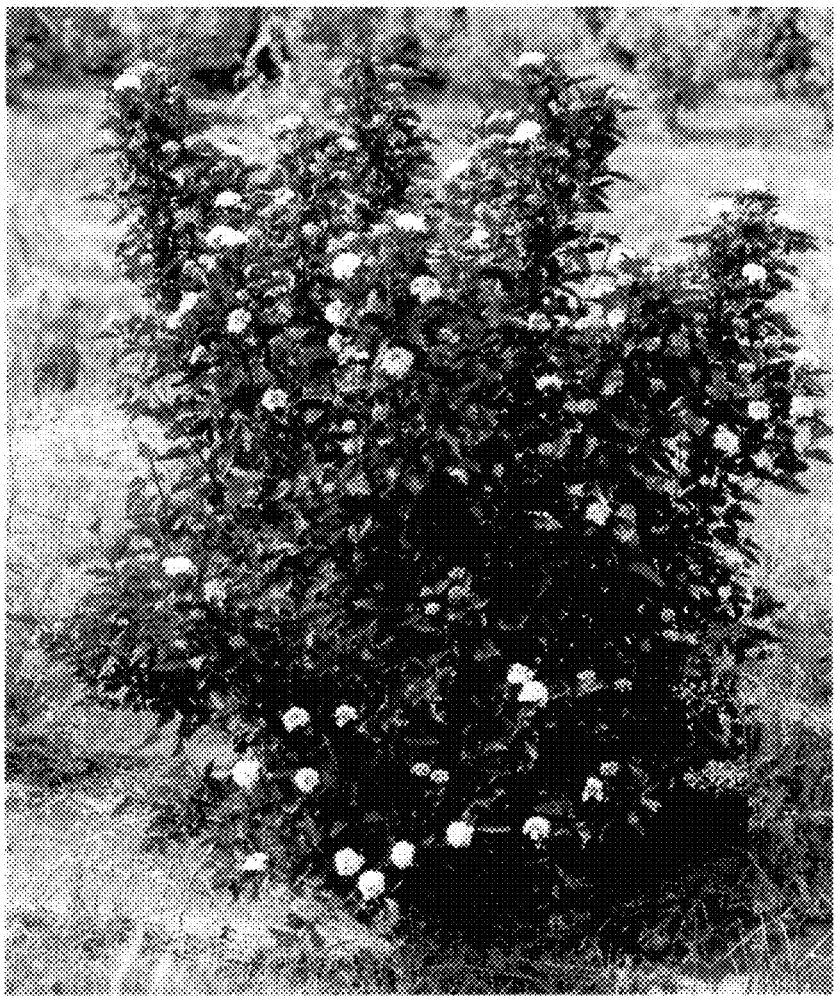

Latin name of genus and species: *Physocarpus opulifolius.*

Cultivar Denomination: 'SMPOCGT'.

BACKGROUND OF THE INVENTION

The new *Physocarpus* cultivar is a product of a planned breeding program conducted by the inventor in Grand Haven, Michigan, to produce *Physocarpus* varieties in new colors and sizes. The open-pollination resulting in this new cultivar was made during the year 2010.

The new *Physocarpus* cultivar resulted from the open-pollination of the seed parent, *Physocarpus* 'Center Glow', U.S. Plant Pat. No. 16,894. The exact pollen parent is unknown. The new cultivar was identified as a potentially interesting selection in the summer of 2013, at a commercial nursery in Grand Haven, Michigan.

Asexual reproduction of the new cultivar 'SMPOCGT' by softwood cuttings was first performed during the summer of 2013, at commercial greenhouse in Grand Haven, Michigan. Subsequent propagation has shown that the unique features of this cultivar are stable and reproduced true to type in 9 successive generations. Date of first sale was Apr. 21, 2023, occurring in Eustis, Maine. This sale was made directly by the inventor or one who obtained the claimed invention directly or indirectly from the inventor. This sale and all public disclosures made between Apr. 21, 2023 and the filing of this application fall within the exception allowed under 102(b)(1).

SUMMARY OF THE INVENTION

The cultivar 'SMPOCGT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMPOCGT'. These characteristics in combination distinguish 'SMPOCGT' as a new and distinct *Physocarpus* cultivar:

1. Very good mildew resistance.
2. Very strong red/orange spring leaf flush, with leaves turning to a dark maroon for summer.
3. Mature leaf underside is green.
4. Bright red stems.
5. Corymbs of light pink to white flowers which produce bright reddish-pink seed heads.

PARENT COMPARISON

Plants of the new cultivar 'SMPOCGT' are similar to plants of the seed parent, in most horticultural characteristics, however, plants of the new cultivar 'SMPOCGT' differ in the following:

1. New leaf flush of the new cultivar is very strong red/orange, while the new leaf flush of the seed parent is maroon with a lime-green and yellow center.
2. Leaf undersides of the new cultivar have a more contrasting green coloring than the leaf undersides of the seed parent.
3. Plants of the new cultivar are resistant to mildew, while plants of the seed parent are not.

COMMERCIAL COMPARISON

Plants of the new cultivar 'SMPOCGT' can also be compared to the commercial cultivar *Physocarpus opulifolius* 'SMNPOBLR', U.S. Plant Pat. No. 28,695. The varieties are similar in most horticultural characteristics; however 'SMPOCGT' differs in the following:

1. Mature leaves of the new cultivar are dark maroon with a green underside, while mature leaves of this comparator are dark maroon with a reddish underside.
2. Plants of the new cultivar are more resistant to powdery mildew than plants of this comparator.

BRIEF DESCRIPTION OF THE PHOTOGRAPHS

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of new *Physocarpus opulifolius* 'SMPOCGT'. Photographs provided by the breeder.

FIG. 1 illustrates in full color the typical plant habit of the new cultivar in a trial field. The plant was grown in Grand Haven, Michigan. Age of the plant is approximately 4 years.

Figure 2:
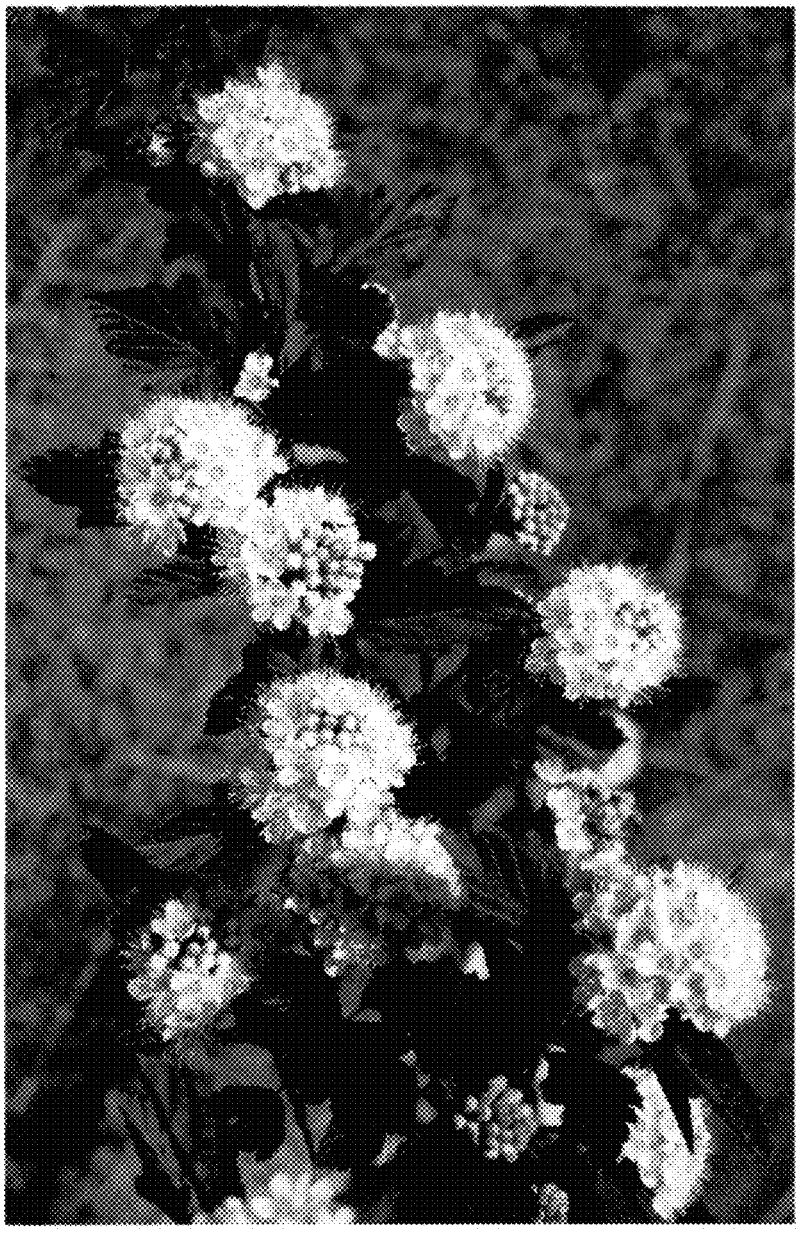

FIG. 2. illustrates in full color a closeup of the open flowers of the new cultivar.

Figure 3:
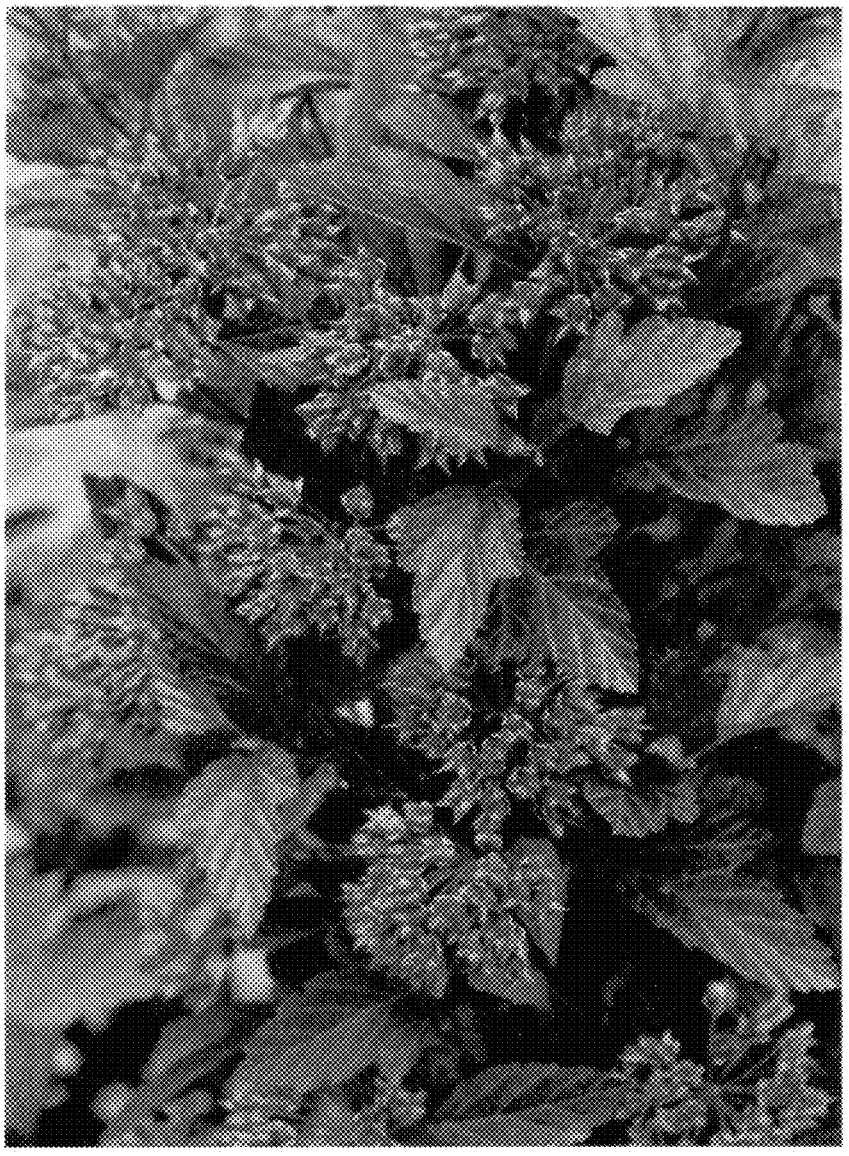

FIG. 3 illustrates in full color seedheads of the new cultivar.

DETAILED BOTANICAL DESCRIPTION

In the following description, color references are made to The Royal Horticultural Society Colour Chart 2015 except where general terms of ordinary dictionary significance are used. The following observations and measurements describe 'SMPOCGT' plants grown in a shaded hoop house in Grand Haven, Michigan. The plants were approximately 2 years old grown in #3 containers. Measurements and numerical values represent averages of typical plant types.

Botanical classification: *Physocarpus opulifolius* 'SMPOCGT'.

PROPAGATION

Time to Initiate Roots: About 25 days at approximately 24° C.

Root Description: Moderate to dense, freely branching, both fibrous and fleshy. White and brown in color, not accurately measured with RHS chart.

Time to Produce a liner: About 60 days at 24° C.

PLANT

Plant type: Flowering perennial shrub.
Age of Plant Described: Approximately 2 years old.
Plant Shape: Upright, mounded, and compact.
Growth Habit: Upwards and outwards.
Pot size of plant described: 3-gallon.
Height: 65 cm.
Plant Spread: 75 cm.
Growth Rate: Fast.
Plant vigor: Good.
Branching Characteristics: Basal; pinching required.
Length of Primary Lateral Branches: 40 cm.
Diameter of Lateral Branches: 4 mm.
Quantity of Lateral Branches: About 100.

Stem:
- *Appearance*.—Rounded, slight pentagonal shape.
- *Aspect /Angle*.—30° to 80°.
- *Strength*.—Strong.
- *Pubescence*.—None.
- *Color*.—RHS Greyed-Orange 176B.

Internode length: 2.5 cm.

FOLIAGE

Leaf:
- *Arrangement*.—Alternate, single.
- *Length*.—7 cm.
- *Width*.—6 cm.
- *Shape of blade*.—Widely ovate. Tri-lobed.
- *Apex*.—Acute.
- *Base*.—Obtuse.
- *Margin*.—Double serrate.
- *Texture of top surface*.—Glabrous.
- *Texture of bottom surface*.—Glabrous with prominent venation.
- *Pubescence*.—None
- *Color*.—Young foliage upper side: RHS Greyed-Orange 166A fading to 166B. Young foliage under side: RHS Greyed-Orange 166A fading to 166B. Mature foliage upper side: RHS Brown 200A to Greyed-Purple 187A. Mature foliage under side: RHS Yellow-Green 148B.
- *Venation*.—Type: Pinnate. Color, upper side: RHS Yellow-Green 148B. Color, under side: RHS Yellow-Green 148B.
- *Petiole*.—Length: 2.5 cm. Diameter: 1.5 mm. Color, upper side: RHS Greyed-Orange 176B. Color, lower side: RHS Greyed-Orange 176B. Texture, upper side: Glabrous/waxy. Texture, lower side: Glabrous/waxy.
- *Stipule*.—Length: 0.5 cm. Diameter: 1.5 mm.

FLOWER

Natural flowering season: April-May.
Inflorescence type and habit: Compact corymb.
Quantity of flowers per inflorescence: 20 to 25.
Quantity of flowers per lateral stem: 10 to 20 inflorescences with about 20 flowers each (200 to 400 individual flowers).
Quantity of buds per lateral stem: Hundreds.
Quantity of buds and flowers per plant: Thousands.
Inflorescence size:
- *Width*.—3 cm.
- *Height*.—2.5 cm.

Individual Flower:
- *Flower form*.—Single whorl.
- *Habit*.—Along lengths of lateral branches, concentrated more heavily at terminal ends.
- *Shape*.—Rotate.
- *Aspect*.—Upright.
- *Diameter*.—1.8 cm.
- *Length*.—0.8 cm.
- *Depth*.—1.8 cm.
- *Persistence*.—Self-cleaning.

Petal:
- *Arrangement*.—Whorl.
- *Quantity*.—5.
- *Appearance*.—Glabrous, opaque.
- *Shape*.—Rounded, obovate.

*Margin*.—Glabrous, entire.
*Tip*.—Rounded.
*Base*.—Obtuse.
*Length*.—0.5 cm.
*Width*.—0.5 cm.
*Texture*.—Upper: Glabrous. Lower: Glabrous.
*Color*.—When opening: Upper surface: RHS Red-Purple 69B. Lower surface: RHS Red-Purple 62D. Fully opened: Upper surface: RHS White 155C. Lower surface: RHS White 155C. Fading: Upper surface: RHS Red-Purple 73D. Lower surface: RHS Red-Purple 73D.

Petaloids: None present.

Bud:
*Shape*.—Round.
*Length*.—2 mm.
*Diameter*.—2 mm.
*Color*.—RHS Red-Purple 73C.

Sepals:
*Shape*.—Broadly triangular.
*Quantity*.—4.
*Arrangement*.—Cruciform.
*Length*.—2 mm.
*Width*.—2 mm.
*Margin*.—Entire.
*Base*.—Truncate.
*Tip*.—Acute.
*Texture*.—Upper: Glabrous. Lower: Glabrous.
*Color*.—Upper side: RHS Yellow-Green 149D. Under side: RHS Yellow-Green 149C with Red-Purple 64B tips.

Calyx:
*Shape*.—Rotate.
*Length*.—4 mm.
*Diameter*.—6 mm.

Peduncle:
*Length*.—0.9 cm.
*Diameter*.—1.5 mm.
*Angle*.—60°.
*Strength*.—Good.
*Texture*.—Glabrous, waxy.
*Color*.—RHS Yellow-Green 147C.

Pedicels:
*Length*.—8 to 10 mm.
*Diameter*.—Less than 1 mm. Color: RHS Yellow-Green 153C.
*Angle*.—60° to 90 °.
*Strength*.—Good.
*Texture*.—Glabrous.

REPRODUCTIVE ORGANS

Stamens:
*Number*.—20.
*Filament length*.—4 mm.
*Filament color*.—RHS White 155B.

Anthers:
*Shape*.—Elliptic, round.
*Length*.—0.5 mm.
*Color*.—RHS Brown 200A.
Pollen: Little to moderate.
Pollen Color: RHS White 155A.

Pistil:
*Number*.—4.
*Length*.—3 mm.
Style.—Length: 3 mm. Color: RHS White 155B.
*Stigma*.—Shape: Club-shaped. Color: RHS Yellow-Green 153D. Ovary color: RHS Yellow-Green 151D.

OTHER CHARACTERISTICS

Fruit: Fruits are comprised of three to four follicles which form per flower; Follicles typically possess 1-2 seeds each; each flower gives rise to 3 to 8 seeds on average.
Quantity.—Several hundred per lateral branch. Length: Measured as one, the follicles comprising the fruit are overall 5 mm in length. Diameter: Measured as one, the follicles comprising the fruit are overall 4 mm in diameter.
*Color*.—RHS Red 42B.
*Texture*.—Glabrous.
*Taste*.—Inedible.

Seeds:
*Length*.—1 mm.
*Diameter*.—0.5 mm.
*Color*.—RHS Orange-White 159A.

Disease/pest resistance: Strong resistance to powdery mildew.

Temperature tolerance: The new cultivar tolerates temperatures between −31 to 38° C. Great tolerance to wind and rain.

What is claimed is:

1. A new and distinct cultivar of *Physocarpus* plant named 'SMPOCGT' as herein illustrated and described.

* * * * *